(12) United States Patent
Gryska et al.

(10) Patent No.: US 9,018,060 B2
(45) Date of Patent: Apr. 28, 2015

(54) VARIABLE CAPACITANCE SENSORS AND METHODS OF MAKING THE SAME

(75) Inventors: Stefan H. Gryska, Woodbury, MN (US); Michael C. Palazzotto, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 122 days.

(21) Appl. No.: 13/703,545

(22) PCT Filed: Jun. 2, 2011

(86) PCT No.: PCT/US2011/038844
§ 371 (c)(1),
(2), (4) Date: Dec. 11, 2012

(87) PCT Pub. No.: WO2011/159480
PCT Pub. Date: Dec. 22, 2011

(65) Prior Publication Data
US 2013/0088244 A1 Apr. 11, 2013

Related U.S. Application Data

(60) Provisional application No. 61/354,843, filed on Jun. 15, 2010.

(51) Int. Cl.
*H01L 21/8242* (2006.01)
*G01R 27/26* (2006.01)
*G01N 27/22* (2006.01)

(52) U.S. Cl.
CPC .......... *G01R 27/2605* (2013.01); *G01N 27/226* (2013.01); *G01N 27/223* (2013.01)

(58) Field of Classification Search
USPC .......... 257/E21.351; 438/171, 190, 210, 239, 438/244, 250, 381, 393
See application file for complete search history.

(56) References Cited

U.S. PATENT DOCUMENTS

| | | | |
|---|---|---|---|
| 4,603,372 A | 7/1986 | Abadie et al. | |
| 5,135,691 A * | 8/1992 | Hama et al. | 264/624 |

(Continued)

FOREIGN PATENT DOCUMENTS

| | | |
|---|---|---|
| CN | 1257052 A | 6/2000 |
| CN | 1321243 A | 11/2001 |

(Continued)

OTHER PUBLICATIONS

Budd, Peter M., et al., *Polymers of intrinsic microporosity (PIMS): robust, solution-processable, organic nanoporous materials*, Chem. Commun., 2004, pp. 230-231.

(Continued)

*Primary Examiner* — Asok K Sarkar
(74) *Attorney, Agent, or Firm* — Bradford B. Wright

(57) ABSTRACT

A variable capacitance sensor includes a first conductive electrode comprising electrically interconnected first conductive sheets; a second conductive electrode comprising electrically interconnected second conductive sheets, wherein the first conductive sheets are at least partially interleaved with the second conductive sheets, and wherein the second conductive electrode is electrically insulated from the first conductive electrode; and microporous dielectric material at least partially disposed between and contacting the first conductive sheets and the second conductive sheets. A method of making a variable capacitance sensor by replacing ceramic in a ceramic capacitor with a microporous material is also disclosed.

8 Claims, 2 Drawing Sheets

(56) References Cited

U.S. PATENT DOCUMENTS

| | | | |
|---|---|---|---|
| 5,143,696 A | | 9/1992 | Haas et al. |
| 5,172,299 A | | 12/1992 | Yamada |
| 5,254,371 A | | 10/1993 | Hegner et al. |
| 5,443,746 A | * | 8/1995 | Harris et al. ............ 252/62.9 R |
| 5,658,444 A | | 8/1997 | Black et al. |
| 5,676,745 A | * | 10/1997 | Kelly et al. ..................... 106/35 |
| 5,771,567 A | * | 6/1998 | Pierce et al. .................... 29/600 |
| 5,951,908 A | * | 9/1999 | Cui et al. ................. 252/62.9 R |
| 5,997,795 A | * | 12/1999 | Danforth et al. ............. 264/401 |
| 6,004,500 A | * | 12/1999 | Safari et al. ................... 264/610 |
| 6,202,471 B1 | | 3/2001 | Yadav |
| 6,222,376 B1 | | 4/2001 | Tenney, III |
| 6,226,172 B1 | | 5/2001 | Sato |
| 6,309,703 B1 | * | 10/2001 | Wapner et al. ................ 427/288 |
| 6,513,362 B1 | * | 2/2003 | Yadav et al. ................. 73/31.05 |
| 6,532,824 B1 | | 3/2003 | Ueno |
| 6,571,603 B1 | | 6/2003 | Doleman et al. |
| 6,746,960 B2 | | 6/2004 | Goodman |
| 6,813,931 B2 | * | 11/2004 | Yadav et al. ................. 73/31.05 |
| 6,938,482 B2 | | 9/2005 | Schultz |
| 7,342,479 B2 | | 3/2008 | Glatkowski et al. |
| 7,449,146 B2 | | 11/2008 | Rakow et al. |
| 7,556,774 B2 | | 7/2009 | Rakow et al. |
| 7,767,143 B2 | | 8/2010 | Wendland et al. |
| 7,892,599 B2 | * | 2/2011 | Yadav et al. ................. 427/212 |
| 8,378,694 B2 | | 2/2013 | David et al. |
| 8,409,511 B2 | | 4/2013 | Thomas et al. |
| 2002/0184939 A1 | * | 12/2002 | Yadav et al. ................. 73/24.04 |
| 2004/0256948 A1 | * | 12/2004 | Solberg ......................... 310/311 |
| 2005/0051763 A1 | * | 3/2005 | Affinito et al. ..................... 257/3 |
| 2006/0246273 A1 | | 11/2006 | Mckeown et al. |
| 2006/0257996 A1 | * | 11/2006 | Simpson et al. ........... 435/287.2 |
| 2007/0141580 A1 | | 6/2007 | David et al. |
| 2008/0063575 A1 | | 3/2008 | Rakow et al. |
| 2008/0093422 A1 | * | 4/2008 | Kodas et al. .................. 228/188 |
| 2008/0160858 A1 | | 7/2008 | Paolucci et al. |
| 2008/0236251 A1 | | 10/2008 | Tepper et al. |
| 2009/0108852 A1 | | 4/2009 | Alimi et al. |
| 2010/0133528 A1 | | 6/2010 | Moon |
| 2010/0277740 A1 | | 11/2010 | Hulteen et al. |
| 2011/0045601 A1 | | 2/2011 | Gryska et al. |
| 2013/0126774 A1 | * | 5/2013 | Venkatesh et al. ....... 252/62.9 R |

FOREIGN PATENT DOCUMENTS

| | | |
|---|---|---|
| JP | 61-237044 A | 10/1986 |
| JP | 63-31361 U | 2/1988 |
| JP | 02-151753 A | 6/1990 |
| JP | H06-18392 A | 1/1994 |
| JP | 10-293107 A | 11/1998 |
| KR | 10-2006-0102236 | 9/2006 |
| NL | 1006268 | 12/1998 |
| WO | WO 99/08105 | 2/1999 |
| WO | WO 2005/012397 | 2/2005 |
| WO | WO 2006/087568 | 8/2006 |
| WO | WO 2009/045733 | 4/2009 |
| WO | WO 2009/046011 | 4/2009 |
| WO | WO 2009/066992 | 5/2009 |
| WO | WO 2010/088088 | 8/2010 |

OTHER PUBLICATIONS

Budd, Peter M., et al. *Polymers of Intrinsic Microporosity (PIMs): High Free Volume Polymers for Membrane Applications*, Macromolecular Symposia, 2006, vols. 245-246, pp. 403-405.

Ghanem et al., *Synthesis, Characterization, and Gas Permeation Properties of a Novel Group of Polymers with Intrinsic Microporosity: PIM—Polyimides*, Macromolecules, 2009, vol. 42, pp. 7881-7888.

McKeown, Neil B., *Polymers of Intrinsic Microporosity (PIMs): Bridging the Void between Microporous and Polymeric Materials*, Chemistry, A European Journal, 2005, 11, pp. 2610-2620.

Freund, Michael S., et al., *A chemically diverse conducting polymer-based "electronic nose"*, Proceedings of the National Academy of Sciences USA, Mar. 1995, vol. 92, pp. 2652-2656.

Dai, Ching-Liang, *A capacitive humidity sensor integrated with micro heater and ring oscillator circuit fabricated by CMOS-MEMS technique*, Sensors and Actuators B: Chemical, vol. 122, Issue 2, Mar. 26, 2007, pp. 375-380.

Zampetti, S., et al., *Design and optimization of an ultra thin flexible capacitive humidity sensor*, Sensors and Actuators B: Chemical, vol. 143, Issue 1, Dec. 4, 2009, pp. 302-307.

International Search Report, PCT/US2011/038844, mailed Sep. 1, 2011, 3 pages.

Sailor, Michael J., Water Sensor Experiment UCSD NanoLab, University of California, San Diego, downloaded from the worldwide web at http://www.google.com/url?sa=t&rct=j&q=&esrc=s&frm=1&source=web&cd=1&ved=0CC0QFjAA&url=http%3A%2F%2Fsailorgroup.ucsd.edu%2Fresearch%2Fsensorexperiments.pdf&ei=XCe6UfOxJefO0wHYiYCoBQ&usg=AFQjCNHfil8mfJfgNFMiqOZSmyhHCacIPw&sig2=WsgzCNat-GlhlXHVeeD1CQ&bvm=bv.47883778,d.dmQ on Jun. 3, 2010, file properties indicate last edit date of Mar. 2003, 6 pages.

* cited by examiner

VARIABLE CAPACITANCE SENSORS AND METHODS OF MAKING THE SAME

TECHNICAL FIELD

This present disclosure relates to organic vapor detection using capacitance-based sensors and processes for their fabrication.

BACKGROUND

Variable capacitance sensors are typically constructed using dielectric materials by parallel plate-type electrodes. Typically, one electrode is conductive and at the same time sufficiently porous so the organic vapors can reach the microporous dielectric material. However, in order to achieve an adequate detection signal it is typically necessary to use sensors with a relatively large areal footprint that must be accommodated; for example, on a printed circuit board.

SUMMARY

In one aspect, the present disclosure provides a method of making a variable capacitance sensor, the method comprising steps:
a) providing a ceramic capacitor comprising:
   a first conductive electrode comprising electrically interconnected first conductive sheets;
   a second conductive electrode comprising electrically interconnected second conductive sheets, wherein the first conductive sheets are at least partially interleaved with the second conductive sheets, and wherein the second conductive electrode is electrically insulated from the first conductive electrode; and
   ceramic material at least partially disposed between and contacting the first conductive sheets and the second conductive sheets; and
b) replacing at least a portion of the ceramic material with an microporous dielectric material, wherein the microporous dielectric material is at least partially disposed between and contacts the first conductive sheets and the second conductive sheets.

In some embodiments, step b) comprises: etching away at least a portion of the ceramic material; and applying the microporous dielectric material to replace at least a portion of the ceramic material removed by etching.

In some embodiments, substantially all of the ceramic material is replaced with the microporous dielectric material. Accordingly, in some embodiments, step b) comprises: etching away substantially all of the ceramic material; and applying the microporous dielectric material to replace of the ceramic material removed by etching.

In some embodiments, the microporous dielectric material comprises a polymer of intrinsic microporosity (PIM).

In another aspect, the present disclosure provides a variable capacitance sensor comprising:
a first conductive electrode comprising electrically interconnected first conductive sheets;
a second conductive electrode comprising electrically interconnected second conductive sheets, wherein the first conductive sheets are at least partially interleaved with the second conductive sheets, and wherein the second conductive electrode is electrically insulated from the first conductive electrode; and
microporous dielectric material at least partially disposed between and contacting the first conductive sheets and the second conductive sheets.

In some embodiments, the microporous dielectric material comprises a polymer of intrinsic microporosity. In some embodiments, the variable capacitance sensor further comprises a ceramic material at least partially disposed between and contacting the first conductive sheets and the second conductive sheets. In some embodiments, the variable capacitance sensor further comprises an encapsulant layer covering a portion of the first and second conductive electrodes.

Advantageously, variable capacitance sensors according to the present disclosure may combine high sensitivity with a low areal footprint; for example, making them suitable for incorporation in miniature sensing devices. In addition, methods according to the present disclosure make it possible to make variable capacitance sensors of high sensitivity at a relatively low price without need of specialized equipment.

As used herein,
the term "microporous" means that the material has a significant amount of internal, interconnected pore volume, with the mean pore size (as characterized, for example, by sorption isotherm procedures) being less than about 100 nm; and
the term "conductive" means electrically conductive.

The foregoing embodiments may be implemented in any combination thereof, unless such combination is clearly erroneous in view of the teachings of the present disclosure. The features and advantages of the present disclosure will be further understood upon consideration of the detailed description as well as the appended claims.

BRIEF DESCRIPTION OF THE DRAWINGS

While the above-identified drawing figures, which may not be drawn to scale, set forth several embodiments of the present disclosure, other embodiments are also contemplated, as noted in the discussion. Like reference numbers have been used throughout the figures to denote like parts.

DETAILED DESCRIPTION

Figure 1:
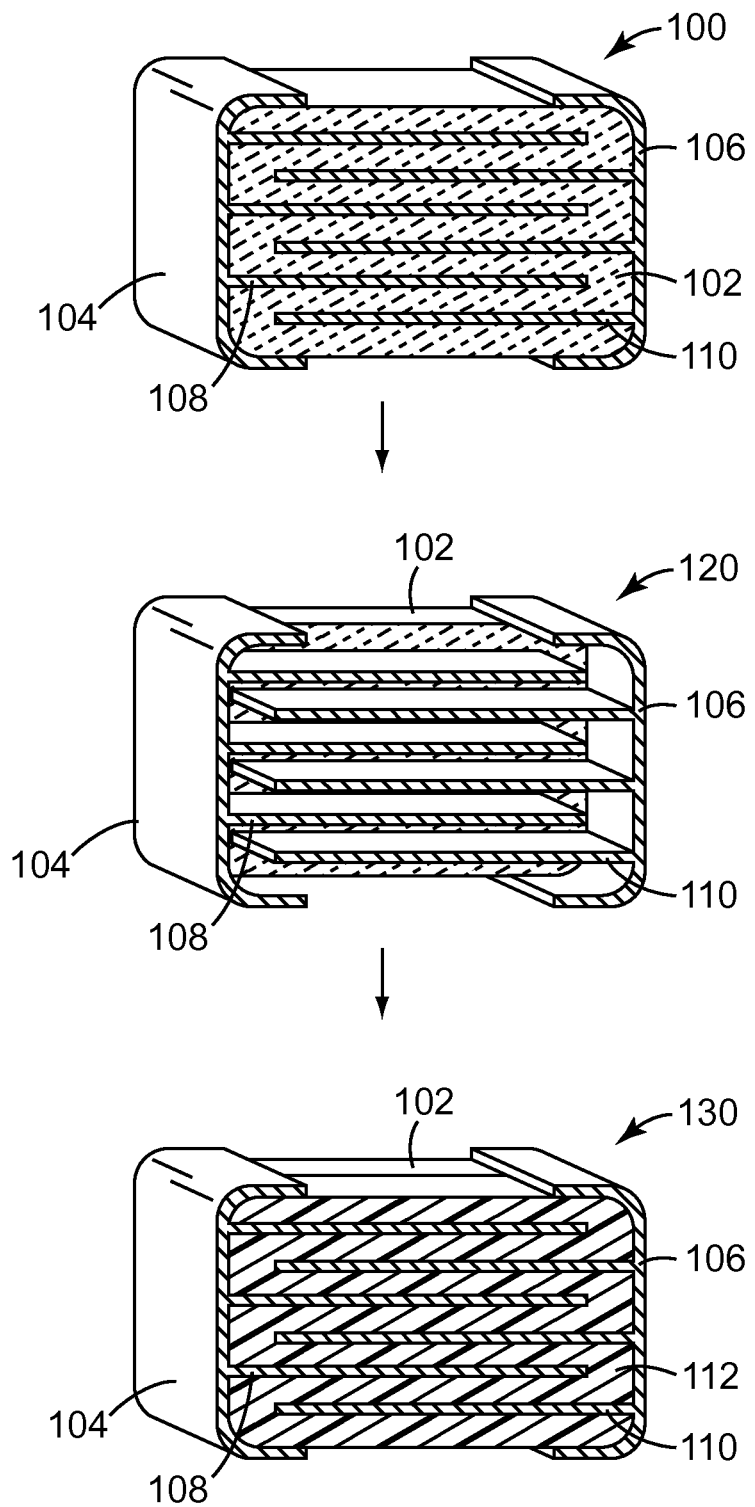
FIG. 1 is a process flow diagram of an exemplary process for making a variable capacitance sensor according to the present disclosure.

Referring now to FIG. 1, in an exemplary process according to the present disclosure a ceramic capacitor 100 is etched to remove at least a portion of the ceramic material 102 separating first and second conductive electrodes 104, 106, respectively, thereby providing etched ceramic capacitor 120. First and second conductive electrodes 104, 106 include first and second conductive sheets 108, 110, respectively. Microporous dielectric material 112 is used to fill in at least a portion of the space originally occupied by etched ceramic material thereby forming variable capacitance sensor 130.

High-quality, low-cost ceramic capacitors are produced by large number of manufacturers. They offer their products in many shapes and sizes, and when purchased in bulk, the price is often pennies per capacitor. Exemplary commercial suppliers include Kemet Corp. of Simpsonville, S.C.; AVX Corporation of Fountain Inn, S.C.; EPCOS Inc. of Munich, Germany; Panasonic Industrial Company of Secaucus, N.J.; and ITW Paktron of Lynchburg, Va. The ceramic capacitor may be obtained with or without an outer protective covering such, for example, as an encapsulant layer.

The first and second conductive electrodes can comprise any suitable conductive material; typically, a conductive metal although or materials may be used. Combinations of different materials (conductive and/or nonconductive) can be used, as different layers or as a mixture, as long as sufficient overall conductivity is provided (e.g., the electrode material may have a constant resistivity of less than about $10^{-2}$ ohms-meter). Examples of conductive materials that can be used to make the first conductive electrode and/or second conductive electrode include metals, alloys, and combinations thereof. Examples include copper, nickel, tin, tantalum, indium-tin oxide, gold, silver, platinum, palladium, titanium, and chromium. In one embodiment, both conductive electrodes comprise the same material; in an alternative embodiment, the first and second conductive electrodes comprise different materials.

In some embodiments according to the present disclosure, the first and second conductive electrodes are included with the ceramic capacitor as obtained. In other embodiments according to the present disclosure, the conductive electrodes are fabricated through a repetitive process with alternating cycles. In one exemplary such cycle, a metal layer (corresponding to a conductive sheet of the first conductive electrode) is deposited on a layer of PIM, then another layer of PIM is deposited on the metal layer. A second metal layer (corresponding to a conductive sheet of the second conductive electrode) is then deposited, offset from the first metal layer, on the PIM layer. Another PIM layer is then deposited on second metal layer, and the entire process is repeated as many times as desired. The PIM lay may be deposited by any suitable printing method such as, for example, screen printing or gravure printing. The metal layers may be deposited by printing; for example, using conductive ink or by vapor coating techniques. The process is repeated as many times as desired. The conductive sheets of each conductive electrode are joined together to form a complete conductive electrode. Joining of the conductive sheets may be accomplished, either during deposition of the conductive sheets, or by applying a conductive material across exposed edges of the conductive sheets. In some cases, heating may be effective to fuse the conductive sheets to a metallic edge strip.

Any ceramic material can be used; typically a dielectric ceramic material. Examples include titanates, zirconates, other metal oxides, and combinations thereof. Common ingredients include titanium dioxide, barium titanate, and strontium titanate.

Referring again to FIG. 1, the ceramic material 102 is at least partially disposed between and contacts conductive sheets 108, 110 of respective first and second conductive electrodes 104, 106.

According to methods of the present disclosure, at least a portion of the ceramic material is replaced with a microporous dielectric material such that each of the ceramic material and the microporous dielectric material are at least partially disposed between and contact the first and second conductive electrodes. Removal of the ceramic material can be effected, for example, by mechanical, laser, and/or chemical techniques. In one embodiment, the ceramic material it etched using a chemical etchant that preferentially etches the ceramic relative to the conductive electrode material. Useful etchants include alkali metal hydroxide solutions in water; optionally in combination with organic solvent. An exemplary etchant is 5 molar sodium hydroxide in water/ethanol (2:1 ratio).

Typically, the etching process may take minutes to days depending on the construction of the ceramic capacitor used. In general, etching occurs at all exposed surfaces of the ceramic material. Hence, in cases wherein a portion of the ceramic material is removed, ceramic material will still be present within the interior of the etched capacitor. If desired, however, substantially all or all of the ceramic material may be removed by etching.

According to methods of the present disclosure, at least a portion of the ceramic material removed by etching is replaced with microporous dielectric material. The function of the microporous dielectric material is to separate the first and second conductive electrodes and provide a receiving substrate for any analytes (e.g., volatile organic compounds) to be sensed. Typically, it is desirable to select a microporous dielectric material with relatively low affinity for water vapor, if the sensor is intended for use under ambient conditions.

The microporous dielectric material may typically be any microporous dielectric material; although for some applications such as sensing particular volatile organic compounds, the choice of microporous dielectric material may enhance or reduce vapor adsorption and/or absorption, and hence sensor sensitivity. For example, the microporous dielectric material may be inorganic or organic, a combination of inorganic and organic components.

Typically, the microporous dielectric material will have a network of intercommunicated pores that extend substantially throughout the microporous dielectric material, although this is not a requirement. Such an arrangement of pores provides a large surface area for adsorption and/or absorption, and provides that molecules of an analyte (if present) will be able to penetrate the internal pores of the material and reside therein. The presence of such analyte in the internal pores can alter the dielectric properties of the material such that a change in the dielectric constant (or any other suitable electrical property) can be observed.

In some embodiments, the microporous dielectric material has a porosity of at least about 10 percent, at least about 20 percent, or at least about 30 percent (as characterized, for example, by sorption isotherm techniques, such as those using instruments available under the trade mark Autosorb from Quantachrome Instruments of Boynton Beach, Fla.). Such porosity can provide good response to low levels of organic chemical analytes. However, the material should not have such a high pore volume that it is difficult to avoid electrical shorting or arcing between the first conductive electrode and the second conductive electrode. Thus, in various embodiments, the material has a porosity of at most about 90 percent, at most about 60 percent or at most about 40 percent.

The microporous dielectric material may, for example, have an average pore size of less about 50 nanometers (nm), less than about 20 nm, or less than about 10 nm. Similarly, the microporous dielectric material may, for example, have an average pore size of greater than about 0.3 nm, greater than about 0.5 nm, or greater than about 1.0 nm.

The microporous dielectric material may, for example, be hydrophobic, hydrophilic, or in-between the two. If the microporous dielectric material is a hydrophobic material, it will not absorb liquid water to an extent that the material swells significantly or otherwise exhibits a significant change in a physical property. Such hydrophobic properties are generally useful in providing an organic analyte sensing element that is relatively insensitive to the presence of water. The microporous dielectric material may however comprise relatively polar moieties; for example, for specific purposes.

The microporous dielectric material typically comprises a continuous matrix, although it may be discontinuous, if desired. Such a matrix is defined as an assembly (e.g. a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g. zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g. a latex), or by coating and drying of a sol-gel mixture, may not comprise a continuous network as defined by applicant. However, if such a latex, sol-gel, etc., layer can be consolidated such that individual particles are no longer discernible, nor is it possible to discern areas of the assembly that were obtained from different particles, such a layer may then meet applicant's definition of a continuous matrix.

Examples of suitable microporous dielectric materials include polymers of intrinsic microporosity (PIMs), although other microporous dielectric materials may also be used.

PIMs can be formulated via the use of any combination of monomers that lead to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the linker are held in non-coplanar orientation.

Many PIMs are known in the art and include, for example, those disclosed in "Polymers of Intrinsic Microporosity (PIMs): Robust, Solution-Processable, Organic Microporous Materials," Budd et al, Chem. Commun., 2004, pp. 230-231; in "Polymers of Intrinsic Microporosity (PIMs)," McKeown et al., Chem. Eur. J., 2005, 11, No. 9, 2610-2620; in "Polymers of Intrinsic Microporosity (PIMs): High Free Volume Polymers for Membrane Applications," Budd et al., Macromol. Symp. 2006, vol. 245-246, 403-405; in "Synthesis, Characterization, and Gas Permeation Properties of a Novel Group of Polymers with Intrinsic Microporosity: PIM-Polyimides," Ghanem et al., Macromolecules 2009, 42, 7881-7888; in U.S. Patent Application Publication 2006/0246273 to McKeown et al.; and in Published PCT Application No. WO 2005/012397 A2 to McKeown et al.

Many PIMs are soluble in common organic solvents and thus are amenable to conventional deposition processes such as coating. In certain embodiments, after a PIM material is deposited (e.g., coated), or otherwise formed so as to comprise an analyte-responsive dielectric layer, the PIM may be crosslinked using a suitable crosslinking agent, for example bis(benzonitrile)palladium(II) dichloride. This process may render the microporous dielectric layer insoluble in organic solvents, and/or may enhance certain physical properties such as durability, abrasion resistance, etc., which may be desirable in certain applications.

PIMs may be blended with other materials. For example, a PIM may be blended with a material that itself is not an analyte-responsive dielectric material. Even though not contributing to an analyte response, such a material may be useful for other reasons. For example, such a material may allow the formation of a PIM-containing layer which has superior mechanical properties and the like. PIMs may be dissolved in a common solvent with the other material to form a homogeneous solution, which may be cast to form a analyte-responsive dielectric blend layer comprising both the PIM and the other polymer(s). PIMs may also be blended with a material that is an analyte-responsive dielectric material (for example, zeolites, activated carbon, silica gel, hypercrosslinked polymer networks and the like). Such materials may comprise insoluble materials that are suspended in a solution comprising a PIMs material. Coating and drying of such a solution/suspension may provide a composite microporous dielectric material.

Examples of other useful microporous dielectric materials include plasma-deposited microporous dielectric layers; for example, as described in PCT Publication No. WO2009/046011 A2 (David et al.).

Without wishing to be bound by theory, variable capacitance sensors according to the present disclosure function by adsorbing and/or absorbing a substance to be detected (i.e., an analyte) into the microporous dielectric layer thereby changing its dielectric constant and hence the capacitance of the variable capacitance sensor.

In some embodiments, some ceramic material remains between the conductive electrodes after the removal/etching step. In such cases, a variable capacitance sensor will be produced that has both ceramic material and microporous dielectric material disposed between the conductive electrodes; typically, in a side-by-side arrangement.

Figure 2:
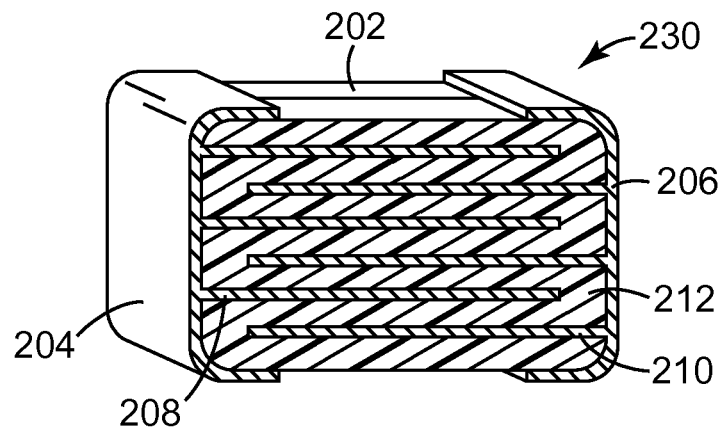
FIG. 2 is a schematic perspective view of an exemplary variable capacitance sensor according to the present disclosure.

Referring now to FIG. 2, an exemplary variable capacitance sensor 230 according to the present disclosure can be prepared by replacing a portion of the ceramic from a ceramic capacitor. Accordingly, variable capacitance sensor 230 comprises first and second conductive electrodes 204, 206 including first and second conductive sheets 208, 210, respectively. Ceramic material 202 and microporous dielectric material 212 are disposed between and contact respective first and second electrodes.

Figure 3:
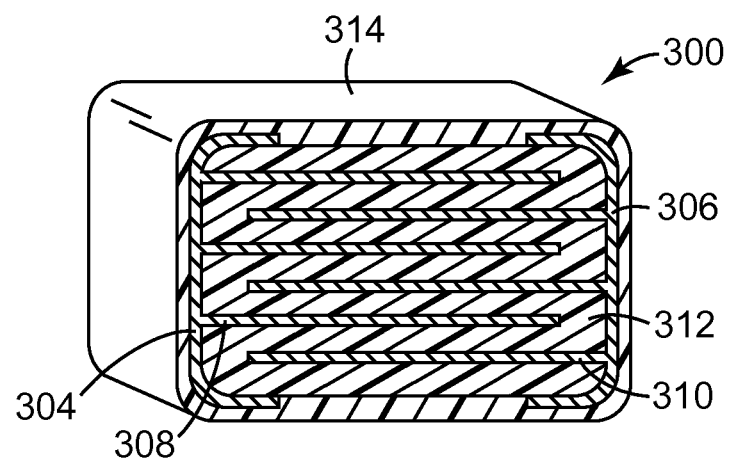
FIG. 3 is a schematic perspective view of an exemplary variable capacitance sensor according to the present disclosure.

Referring now to FIG. 3, an exemplary variable capacitance sensor 330 according to the present disclosure can be prepared by completely replacing the ceramic from a ceramic capacitor. Accordingly, variable capacitance sensor 330 comprises first and second conductive electrodes 304, 306 including first and second conductive sheets 308, 310, respectively. Microporous dielectric material 312 is disposed between and contacts respective first and second electrodes. Optional encapsulant layer 314 covers a portion of first and second conductive electrodes 304, 306.

Optionally, variable capacitance sensors according to the present disclosure may have leads affixed thereto, or they may be used without leads; for example, by clamping them between contacts on a circuit board. Similarly, variable capacitance sensors according to the present disclosure may have a protective cover material over at least a portion of its surface; for example to protect the microporous dielectric material from contamination or damage. However, the inclusion of a covering material must still permit an intended analyte to access the microporous dielectric material in order for the variable capacitance sensor to function properly. Examples of covering material include nonwovens and porous membranes.

Variable capacitance sensors prepared according to the present disclosure are suitable for use in electronic sensing devices. Generally, this involves electrically connecting the variable capacitance sensor to monitoring circuitry that can determine to capacitance of the variable capacitance sensor.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of PIM1

PIM material (PIM1) was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 100.00 grams of 5,5',6,6'-tetrahydroxy-3,3,3',3'-tetramethyl-1,1'-spirobisindane were combined with 59.219 g of tetrafluoroterephthalonitrile, 243.6 g potassium carbonate, and 2543.6 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from ethanol, and air dried at room temperature. A yellow solid product was obtained having a number-average molecular weight of approximately 40,800, as determined by gel permeation chromatography analysis using light scattering detection.

Example 1 a) A commercial 22-nF (22-nanofarad) ceramic capacitor (part #C340C223J2G5CA from Kemet Electronics Corporation, Greenville, S.C.) was cut in two near the wire leads (resulting in a capacitance of 0.488 nF) using a low speed diamond saw in a direction substantially perpendicular to the wire leads. The capacitor had 24 interdigitated metal fingers with a 35 micron pitch and separated by ceramic layers. The portion having the wire leads attached was used in the following procedure. As a control step to show that the comparative capacitance sensor prepared above is operational, the sensor was baked for one hour at 150° C., before it was placed inside a test chamber and exposed to several levels of relative humidity. The sensor showed a high response to humidity, achieving a $\Delta C/C_O$ (i.e., the change in capacitance from the initial value divided by the initial value) value of 0.25 at 80 percent relative humidity. In a separate experiment, the sensor was substantially non-responsive when exposed to acetone vapor introduced into the test chamber (i.e., $\Delta C/C_O$ was essentially zero). The sensor was then was baked for one hour at 150° C., and placed inside the test chamber. Exposure to acetone vapor with concentrations up to at least 4000 ppm showed no change in capacitance ((i.e., $\Delta C/C_O$ was essentially zero).

b) The capacitance sensor made in a) was soaked in 5M sodium hydroxide in water/ethanol (2:1 ratio) solution for 6 days. After soaking, the sensor was carefully washed in distilled water, and dried to remove any residue. It was observed that a small amount of the ceramic was removed, and most of the ceramic was still present. To determine how the etching affected the ceramic sensor the baseline capacitance before and after soaking in the sodium hydroxide solution was compared. The capacitance changed from 488 to 367 pF. To show that the change was not just damage to the sensor, but rather a systematic removal of the ceramic material another humidity test was run with the sensor. After one hour at 150° C. in the oven the sensor was placed inside a test chamber and exposed to several levels of percent relative humidity. The etched capacitance sensor showed a high response to humidity, achieving a $\Delta C/C_O$ (i.e., the change in capacitance from the initial value divided by the initial value) value of 6.6 at 80 percent relative humidity. Clearly, the etched capacitor was much more sensitive to humidity than the non-etched one. Exposure to acetone vapor with concentrations up to at least 4000 ppm showed no change in capacitance ((i.e., $\Delta C/C_O$ was essentially zero).

c) A four percent solution of a PIM1. The solution was prepared in chlorobenzene by mixing the components in a vial and placing it on a roller mill overnight to complete the dissolution of the materials and then filtered through one micrometer pore size filter. The PIM1 solution was applied directly on the etched surface the etched capacitance sensor prepared in b) using a small artist's brush, and then dried for one hour in a 100° C. oven. This procedure was repeated twice. The resultant variable capacitance sensor was tested for response to acetone vapors. After baking for one hour at 150° C., the sensor was placed inside a test chamber, and exposed to acetone vapor. At an acetone vapor concentration of 4000 ppm, the capacitance sensor exhibited a $\Delta C/C_O$ of 0.0012, with detectable differences in capacitance observed at acetone levels of 50 ppm or less. Clearly, by replacing just a portion of the ceramic layer with absorbing microporous material like the PIM in this example, we were able to increase the sensitivity of the variable capacitance sensor toward acetone.

All patents and publications referred to herein are hereby incorporated by reference in their entirety. All examples given herein are to be considered non-limiting unless otherwise indicated. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A variable capacitance sensor comprising:
    a first conductive electrode comprising electrically interconnected first conductive sheets;
    a second conductive electrode comprising electrically interconnected second conductive sheets, wherein the first conductive sheets are at least partially interleaved with the second conductive sheets, and wherein the second conductive electrode is electrically insulated from the first conductive electrode;
    a ceramic material at least partially disposed between and contacting the first conductive sheets and the second conductive sheets; and
    microporous dielectric material at least partially disposed between and contacting the first conductive sheets and the second conductive sheets.

2. The variable capacitance sensor of claim 1, wherein the microporous dielectric material comprises a polymer of intrinsic microporosity.

3. The variable capacitance sensor of claim 1, further comprising an encapsulant layer covering a portion of the first and second conductive electrodes.

4. A method of making a variable capacitance sensor, the method comprising steps:
    a) providing a ceramic capacitor comprising:
        a first conductive electrode comprising electrically interconnected first conductive sheets;
        a second conductive electrode comprising electrically interconnected second conductive sheets, wherein the first conductive sheets are at least partially interleaved with the second conductive sheets, and wherein the second conductive electrode is electrically insulated from the first conductive electrode; and
        ceramic material at least partially disposed between and contacting the first conductive sheets and the second conductive sheets; and b) replacing at least a portion of the ceramic material with a microporous dielectric material, wherein the microporous dielectric material is at least partially disposed between and contacts the first conductive sheets and the second conductive sheets.

5. The method of claim 4, wherein step b) comprises:
etching away at least a portion of the ceramic material; and
applying the microporous dielectric material to replace at least a portion of the ceramic material removed by etching.

6. The method of claim 4, wherein substantially all of the ceramic material is replaced with the microporous dielectric material.

7. The method of claim 6, wherein step b) comprises:
etching away substantially all of the ceramic material; and
applying the microporous dielectric material to replace of the ceramic material removed by etching.

8. The method of claim 4, wherein the microporous dielectric material comprises a polymer of intrinsic microporosity.

\* \* \* \* \*